(12) United States Patent
Stafford

(10) Patent No.: US 11,675,311 B2
(45) Date of Patent: *Jun. 13, 2023

(54) EYE TRACKING SYSTEM WITH HOLOGRAPHIC FILM DECODER

(71) Applicant: Sony Interactive Entertainment Inc., Tokyo (JP)

(72) Inventor: Jeffrey R. Stafford, San Mateo, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 233 days.

This patent is subject to a terminal disclaimer.

(21) Appl. No.: 17/121,735

(22) Filed: Dec. 14, 2020

(65) Prior Publication Data

US 2021/0096645 A1 Apr. 1, 2021

Related U.S. Application Data

(63) Continuation of application No. 16/012,022, filed on Jun. 19, 2018, now Pat. No. 10,866,634.

(51) Int. Cl.
| | |
|---|---|
| *G03H 1/02* | (2006.01) |
| *G06F 3/01* | (2006.01) |
| *G06T 15/20* | (2011.01) |
| *G02B 27/01* | (2006.01) |
| *A61B 3/113* | (2006.01) |
| *G02B 5/32* | (2006.01) |
| *G06V 40/18* | (2022.01) |
| *G06V 10/82* | (2022.01) |
| *G06V 10/147* | (2022.01) |
| *G06V 10/145* | (2022.01) |
| *G06V 40/19* | (2022.01) |

(52) U.S. Cl.
CPC .......... *G03H 1/0248* (2013.01); *A61B 3/113* (2013.01); *G02B 5/32* (2013.01); *G02B 27/0172* (2013.01); *G03H 1/0252* (2013.01); *G06F 3/013* (2013.01); *G06T 15/20* (2013.01); *G06V 10/145* (2022.01); *G06V 10/147* (2022.01); *G06V 10/82* (2022.01); *G06V 40/18* (2022.01); *G06V 40/19* (2022.01); *G02B 2027/0174* (2013.01)

(58) Field of Classification Search
None
See application file for complete search history.

(56) References Cited

U.S. PATENT DOCUMENTS

| | | |
|---|---|---|
| 6,330,088 B1 | 12/2001 | Klug et al. |
| 10,078,219 B2 | 9/2018 | Alexander et al. |

(Continued)

*Primary Examiner* — Jennifer D. Carruth
(74) *Attorney, Agent, or Firm* — John L. Rogitz

(57) ABSTRACT

A volume holographic film (such as a photopolymer) that is pre-recorded with patterns subsequently is used to encode LED or low-power laser light reflections from an eye into a binary pattern that can be read at very high speeds by a relatively simple complementary metal-oxide-semiconductor (CMOS) sensor that may be similar to a high framerate, low resolution mouse sensor. The low-resolution mono images from the film are translated into eye poses using, for instance, a look up table that correlates binary patterns to X, Y positions or using a pre-trained convolutional neural network to robustly interpret many variations of the binary patterns for conversion to X, Y positions.

20 Claims, 12 Drawing Sheets

(56) References Cited

U.S. PATENT DOCUMENTS

| | | |
|---|---|---|
| 10,866,634 B2 * | 12/2020 | Stafford ............. G02B 27/0172 |
| 2012/0002257 A1 | 1/2012 | Shirakura et al. |
| 2015/0205399 A1 | 7/2015 | Kim |
| 2016/0042262 A1 | 2/2016 | Tanaka et al. |
| 2016/0209657 A1 | 7/2016 | Popovich et al. |
| 2016/0349514 A1 | 12/2016 | Alexander et al. |
| 2017/0115487 A1 | 4/2017 | Travis |
| 2017/0286659 A1 | 10/2017 | Xiao |
| 2018/0113418 A1 | 4/2018 | Stafford |
| 2018/0314416 A1 | 11/2018 | Powderly et al. |
| 2020/0103980 A1 | 4/2020 | Katz et al. |
| 2020/0142495 A1 | 5/2020 | Steinberg et al. |
| 2020/0159030 A1 * | 5/2020 | Ayres ................. G02B 27/0172 |

* cited by examiner

EYE TRACKING SYSTEM WITH HOLOGRAPHIC FILM DECODER

FIELD

The application relates generally to eye tracking systems with holographic film decoders.

BACKGROUND

Many applications use eye tracking for useful purposes, such as presenting certain views or user interfaces based on the direction a person is looking. As but one example of the use of eye tracking is presented in the present assignee's USPP 2018/0096518, titled "FIELD OF VIEW (FOV) THROTTLING OF VIRTUAL REALITY (VR) CONTENT IN A HEAD MOUNTED DISPLAY".

As understood herein, when executing eye tracking multiple considerations can compete with each other. For example, it is desirable both to use little power and relatively low computational resources while still providing very high speed and accurate eye tracking.

SUMMARY

Accordingly, in some example embodiments a volume holographic material (such as a photopolymer film) is used to encode LED or ultra low-power laser light reflections from an eye into a binary pattern that can be read at very high speeds by a relatively simple complementary metal-oxide-semiconductor (CMOS) sensor that may be similar to a high framerate, low resolution mouse sensor.

In example implementations, a pre-recorded holographic film is used to decode the infrared LED or ultra-low power laser light into pixel-aligned binary patterns onto a very high framerate (>1000 Hz), low resolution (<64x64 pixels) sensor using a simple processor such as an application specific integrated circuit (ASIC) or microcontroller unit (MCU) embedded onto the sensor. The holographic film performs the tasks typically associated with computer vision processes, which is the classification of an image of the eye to pose values. The ASIC/MCU translates the low-resolution mono images into eye pupil pose information that is relative to the sensor. The embedded ASIC/MCU can use either a look up table that correlates binary patterns from the sensor image to pose values, or a pre-trained convolutional neural network (CNN) classifier, or any other machine learned classifier to robustly interpret many variations of the binary patterns for conversion to pose values. "Pose" refers to the location of the eye and the orientation (direction) in which it is looking, typically as indicated by the pupil. Eye pose indicates direction of gaze of a user, which can be input as eye tracking to computer software, e.g., a computer game.

Accordingly, in an example, a method includes directing light from an encoding laser onto a human eye, which reflects the light onto a holographic film to establish coded emissions on respective regions of the film. The reflected light from the eye establishes reference light that impinges on the holographic film and to produce object light by the process of interference of the reference light with particles (typically silver halide) in the film, which establishes a binary code image corresponding to the eyeball pose.

Subsequently, e.g., during eye tracking for game play, the film is illuminated using at least one reflection of light from a person's eye. The film can be juxtaposed with at least one sensor to sense light from areas of the film illuminated by the reflection of light from a person's eye and representing at least one of the coded emissions. The method includes decoding signals from the sensor representing the at least one coded emission to return a respective position of the eye.

In some implementations, light from the reflection of light from a person's eye is infrared (IR). In non-limiting examples, the sensor includes at least one complementary metal-oxide-semiconductor (CMOS) sensor. In example embodiments, the method may be executed at least in part by a processor that can be implemented by, e.g., application specific integrated circuit (ASIC) or microcontroller unit (MCU). The processor may be embedded onto/into the sensor.

In another aspect, an apparatus includes at least one light source and at least one holographically recorded film having plural coded regions, with each coded region representing a code different from other coded regions on the film. The apparatus also includes at least one sensor to sense light from at least one coded region of the film illuminated by a reflection from an eye of light from the light source. At least one decoder is configured for decoding signals from the sensor representing the at least one coded region to return a respective position of the eye.

In another aspect, an apparatus includes at least one holographically recorded film having plural coded regions. Each coded region represents a code different from other coded regions on the film. One or more data storage media and/or computing units correlate the coded regions to respective positions of an eye. In some other non-limiting implementations, the holographic material could be a thin hologram, a surface relief hologram or other forms of material structure to perform light interference. In addition, reflective holograms can be used instead of transmissive holograms. For simplicity, but without limitations, the present application will refer to thick volume transmission holograms within a photopolymer film containing silver halide crystals as holographic film.

The details of the present application, both as to its structure and operation, can best be understood in reference to the accompanying drawings, in which like reference numerals refer to like parts, and in which:

BRIEF DESCRIPTION OF THE DRAWINGS

FIGS. 2-5 are schematic views of various types of example robust codes that can be established by the reflectors shown in FIG. 1;

FIG. 6 is a block diagram of the encoding laser in a second position, illuminating a second coded reflector, with the motor and mechanism for moving the laser removed for clarity;

FIG. 7 schematically illustrates a data structure that correlates laser positions to specific codes;

FIG. 8 is a block diagram of an encoding laser in a reflective configuration;

FIG. 10 is a flow chart of example logic for establishing the robust codes on the holographic film;

DETAILED DESCRIPTION

This disclosure relates generally to computer ecosystems including aspects of consumer electronics (CE) device networks such as but not limited to computer game networks. A system herein may include server and client components, connected over a network such that data may be exchanged between the client and server components. The client components may include one or more computing devices including game consoles such as Sony PlayStation® or a game console made by Microsoft or Nintendo or other manufacturer of virtual reality (VR) headsets, augmented reality (AR) headsets, portable televisions (e.g. smart TVs, Internet-enabled TVs), portable computers such as laptops and tablet computers, and other mobile devices including smart phones and additional examples discussed below. These client devices may operate with a variety of operating environments. For example, some of the client computers may employ, as examples, Linux operating systems, operating systems from Microsoft, or a Unix operating system, or operating systems produced by Apple Computer or Google. These operating environments may be used to execute one or more browsing programs, such as a browser made by Microsoft or Google or Mozilla or other browser programs that can access websites hosted by the Internet servers discussed below. Also, an operating environment according to present principles may be used to execute one or more computer game programs.

Servers and/or gateways may include one or more processors executing instructions that configure the servers to receive and transmit data over a network such as the Internet. Or, a client and server can be connected over a local intranet or a virtual private network. A server or controller may be instantiated by a game console such as a Sony PlayStation®, a personal computer, etc.

Figure 14:
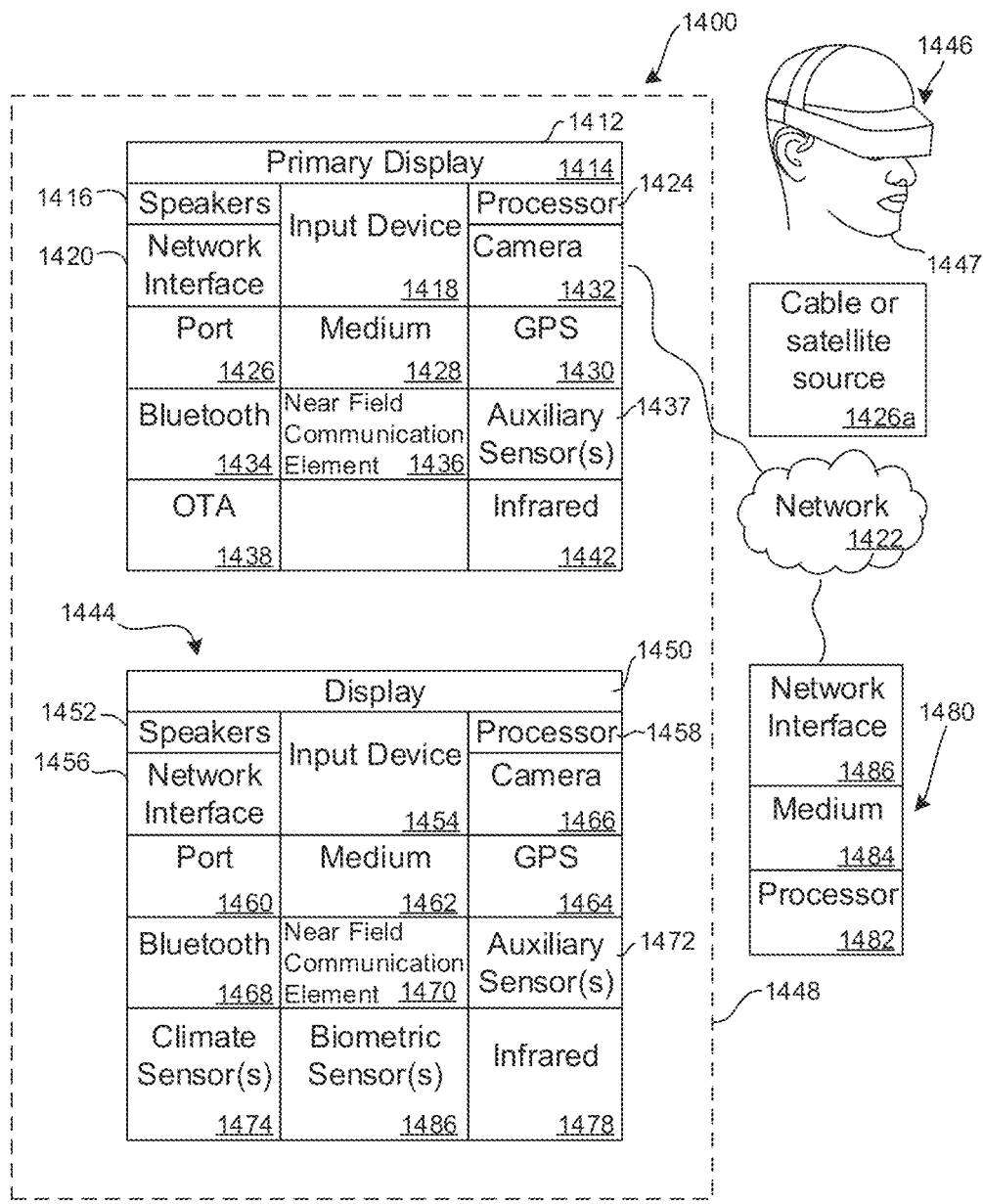
FIG. 14 is a block diagram of an example system in accordance with present principles.

Information may be exchanged over a network between the clients and servers. To this end and for security, servers and/or clients can include firewalls, load balancers, temporary storages, and proxies, and other network infrastructure for reliability and security. One or more servers may form an apparatus that implement methods of providing a secure community such as an online social website to network members. FIG. 14 described below provides example components that may be used herein in the appropriate combinations.

As used herein, instructions refer to computer-implemented steps for processing information in the system. Instructions can be implemented in software, firmware or hardware and include any type of programmed step undertaken by components of the system.

A processor may be any conventional general-purpose single- or multi-chip processor that can execute logic by means of various lines such as address lines, data lines, and control lines and registers and shift registers.

Software modules described by way of the flow charts and user interfaces herein can include various sub-routines, procedures, etc. Without limiting the disclosure, logic stated to be executed by a particular module can be redistributed to other software modules and/or combined together in a single module and/or made available in a shareable library.

Present principles described herein can be implemented as hardware, software, firmware, or combinations thereof; hence, illustrative components, blocks, modules, circuits, and steps are set forth in terms of their functionality.

Further to what has been alluded to above, logical blocks, modules, and circuits described below can be implemented or performed with a general-purpose processor, a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

The functions and methods described below, when implemented in software, can be written in an appropriate language such as but not limited to Java, C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hardwired cables including fiber optic and coaxial wires and digital subscriber line (DSL) and twisted pair wires. Such connections may include wireless communication connections including infrared and radio.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Figure 1:
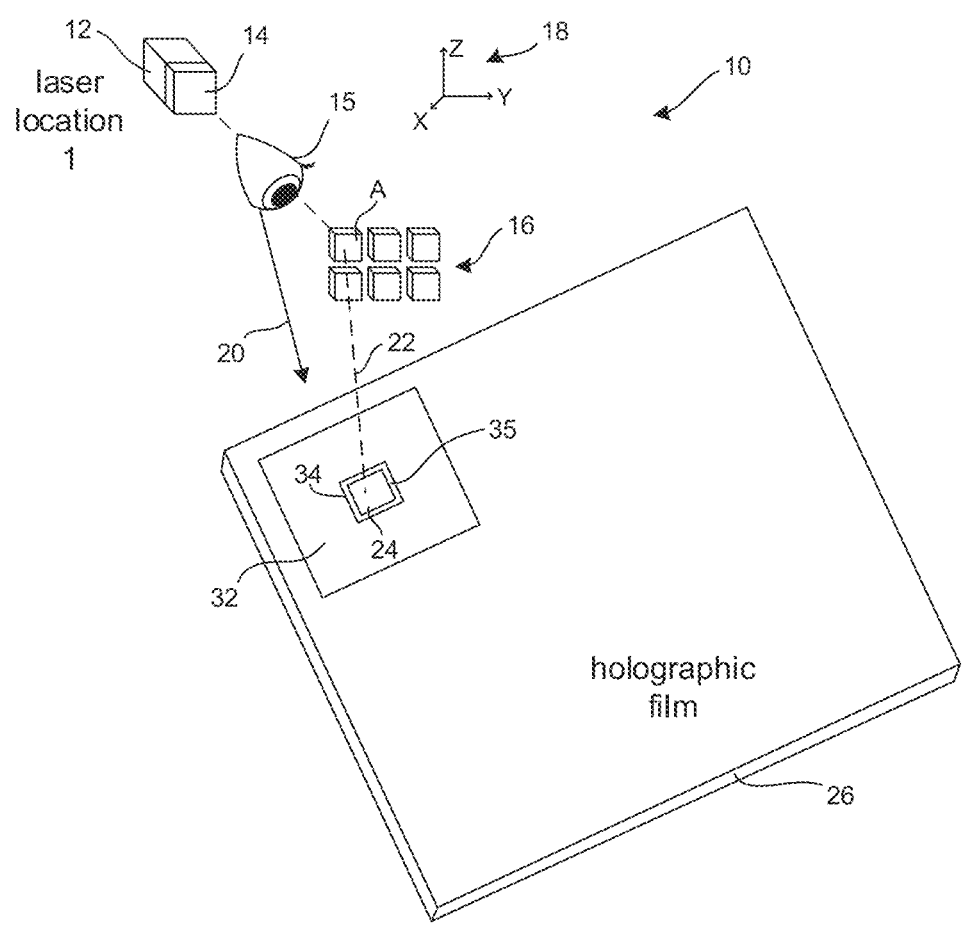
FIGS. 1-8 and 10 depict example methods for pre-recording a holographic film, with FIG. 1 being a block diagram of an encoding laser in a first position, illuminating a first coded reflector.

FIG. 1 illustrates a system 10 that includes one or more encoding lasers 12 that may emit light through one or more adjustable polarizers 14 onto a reference or calibration human or mechanical eyeball 15, which in turn reflects light onto a selected reflector A in an array 16 of reflectors. The polarizers 14 can be optional. Each eyeball position may deflect light onto a reflector in the array 16 to establish, when interacting with reference light described further below, an interference pattern, such as a binary pattern, of light deflection that creates a robust code corresponding to the pose of the eye that produced the interference pattern on the particular area of film. It should also be appreciated that instead of a mechanical eyeball, a digital simulation of an eyeball can be utilized and realized through the use of a spatial light modulator such as a Liquid Crystal on Silicon display device typically referred to as LCOS. The LCOS spatial light modulator or any other spatial light modulator can be used to reflect the encoding laser light to produce a holographic projection of the simulated eyeball, such that it approximates the reflected light from a real or mechanical eyeball.

As understood herein, the process of recording similar interference patterns (due to similar eye poses) between adjoining areas on the holographic film may produce similar binary coded images such that it would be difficult to determine the correct eye pose. In such a case, altering the polarization of the light during the recording process can increase the signal uniqueness of the light from each similar eye pose to each neighboring recording area on the holographic film. When polarizers are used, if the laser/LED light source's polarization state is sequentially changed and the sensor has sufficient frame rate, multiple alternating polarization state frames can be used before determining the actual eyeball pose. For example, if the sensor frame per second (FPS) is 240 hz, an "S" Polarization state can be used for frame 0 and a "P" Polarization state can be used for frame 1. At the end of frame 1, the results of the binary patterns from frame 0 and frame 1 are compared and the frame with the largest correlation (based on sensor pixel intensities) of binary patterns to prerecorded values (for example, via lookup table or CNN classifier) is used for a result at a frame rate of 120 hz.

It should be noted that the use of altering light polarization to improve binary image decoding is just one example, other methods could include altering the wavelength of the light or by using light sources from differing positions and orientations.

In the example shown the eyeball positions are shown reflecting onto a two-dimensional array of mirrors, but they could be reflected onto a three-dimensional array of transparent objects as shown by the x-y-z axes 18. Alternatively, other forms of light reflectors or light diffracting objects can be used, including but not limited to a LCOS spatial light modulator. Reference light 20 from the encoding laser 12 that does not impinge on a reflector can interfere with object light 22 from the calibration eyeball, with the resulting interference pattern being encoded in a region 24 of a holographic film 26. Once illumination of a first eyeball pose "A" is encoded onto the region 24 of the film 26, the eyeball changes pose and the holographic film 26 is moved to expose a different region under the aperture mask 34 to illuminate another one of the areas of the film, establishing its own unique code.

Figure 2:
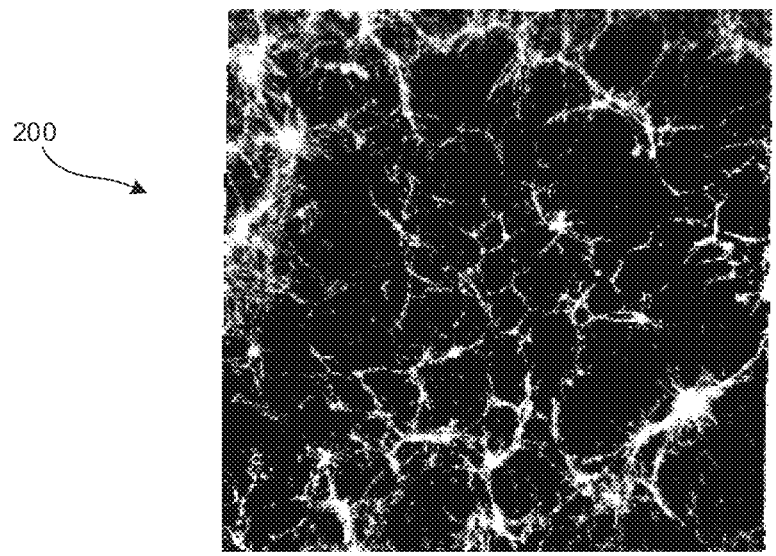
Figure 3:
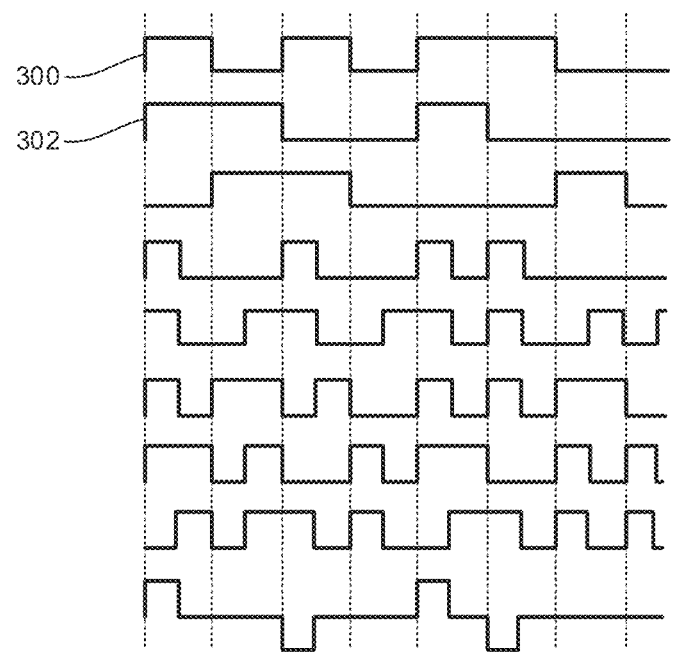
Figure 4:
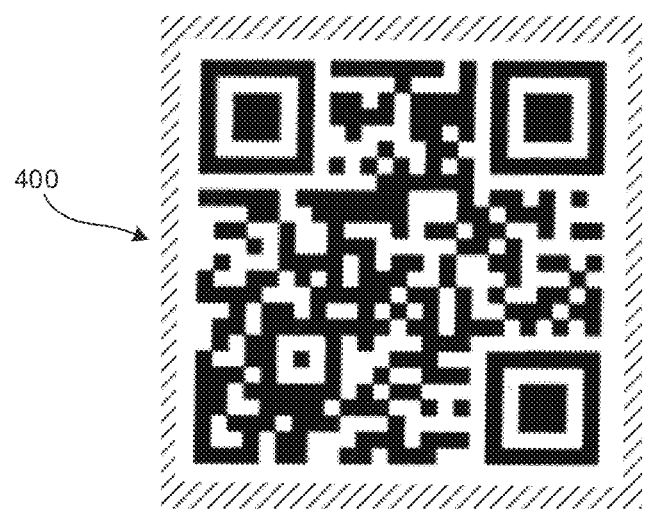
Figure 5:
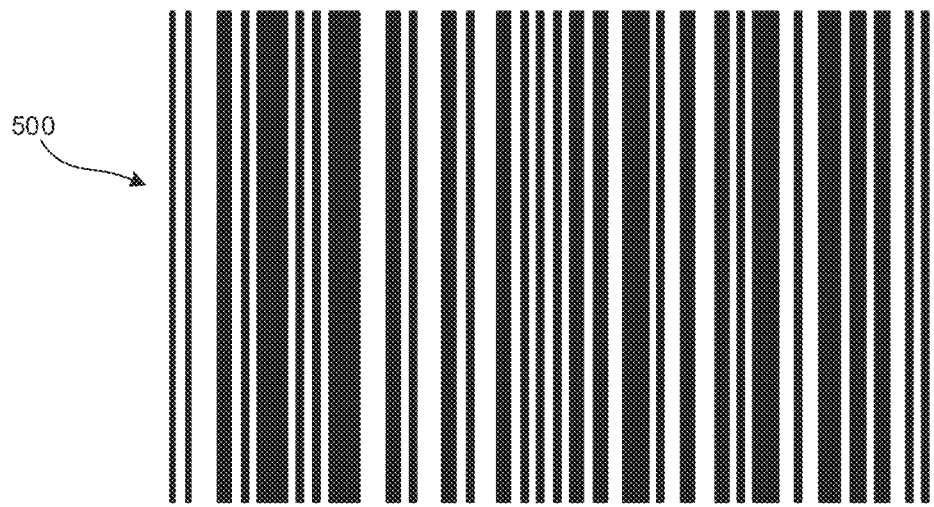

Prior to further explanation of present techniques, reference is directed to FIGS. 2-5, which illustrate various non-limiting examples of robust unique codes that can be established and encoded in its own respective region of the film 26. FIG. 2 shows a single "splotch" 200 with a unique configuration. Each eyeball pose may encode its own respective splotch. FIG. 3 shows a series of unique linear codes, e.g., first and second codes 300, 302 that can be established by respective eyeball poses. FIG. 4 illustrates that each unique code may be a quick response (QR) code 400, while FIG. 5 shows that each unique code may be a bar code 500. Combinations of the codes in FIGS. 2-5 may be used.

The location (also referred to herein as "position") of the encoding laser 12 is in with respect to the film 26 when irradiating the reference eyeball to encode the interference pattern in the region 24 by recording onto the film, the interference pattern being formed from the reflection of the laser light due to the pose of the eyeball (the position of the eyeball and the direction in which the pupil is directed relative to the center of the eye) and the reflection off the objects that create the unique code.

Figure 6:
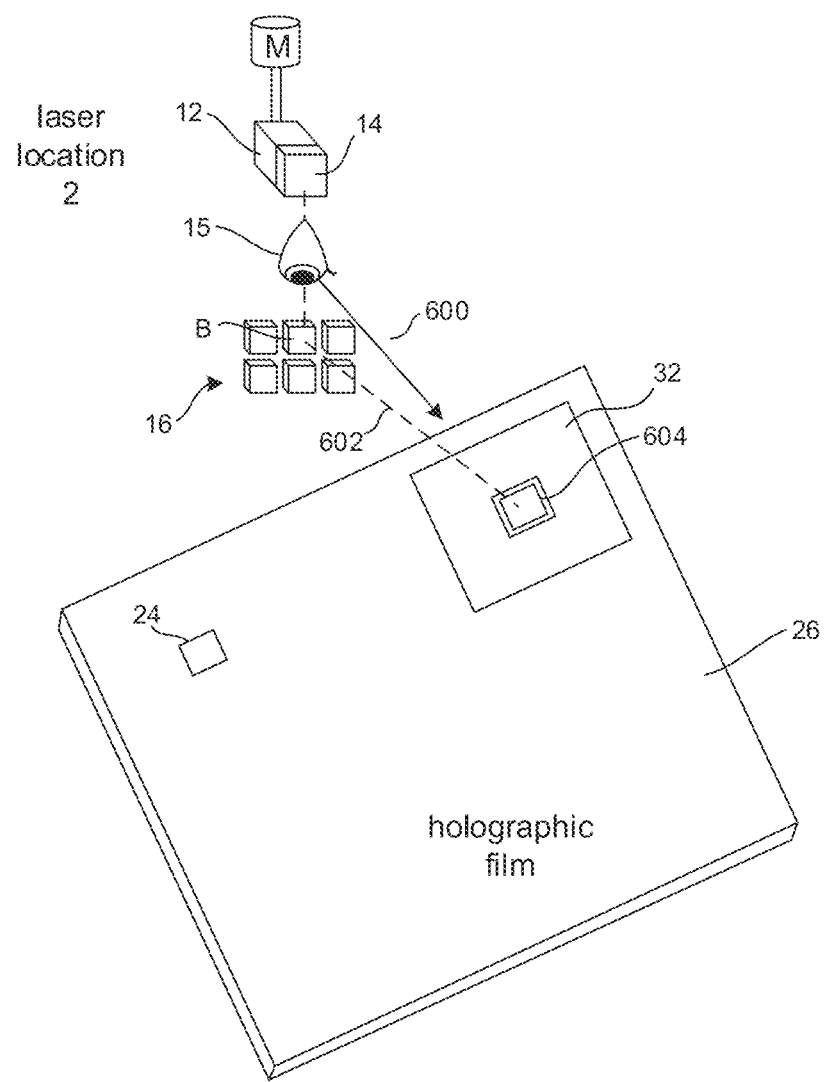

As shown in FIG. 6, once the region 24 has encoded the unique fringe pattern from the eyeball orientation A, the reference, calibration, mechanical or digitally simulated eyeball 15 is moved, e.g., rotated, such that the resulting interference pattern from the direct beam 600 and deflected beam 602 is encoded in a second region 604 that is significantly distanced from the first region 24. As mentioned for FIG. 1, the region 604 under light exposure from the beams 600 and 602, may be due to the holographic film 26 being moved. In the example shown, while the first and second regions encode respective unique codes that are associated with respective eyeball poses that are only a single increment of location recording apart, they may be physically separated from each other by regions of the film 26 that encode other codes associated with other eyeball poses. Also, successive eyeball poses may be irradiated with respective different polarizations. In this way, when the film 26 subsequently is used to determine the pose of a different human eyeball during, e.g., game play or for other eye tracking applications as described more fully below, discrimination of the precise location of the eyeball is made more robust by reducing the possibility of cross-talk caused by similar poses of the eyeball light reflections illuminating similar encodings on the holographic film.

Figure 7:
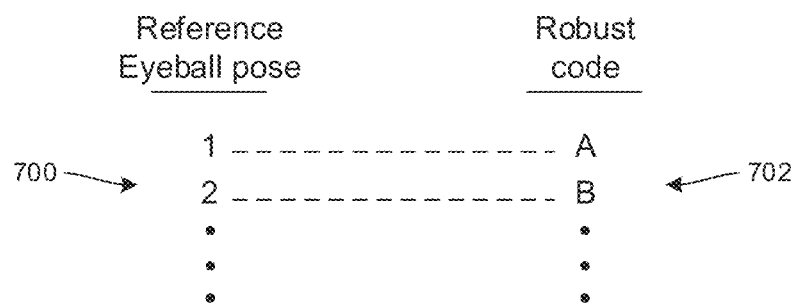

FIG. 7 shows an example data structure that may be recorded on, e.g., disk-based or solid-state memory in which laser locations in a first column 700 are correlated with respective robust codes in a column 702, for purposes to be shortly disclosed.

Figure 8:
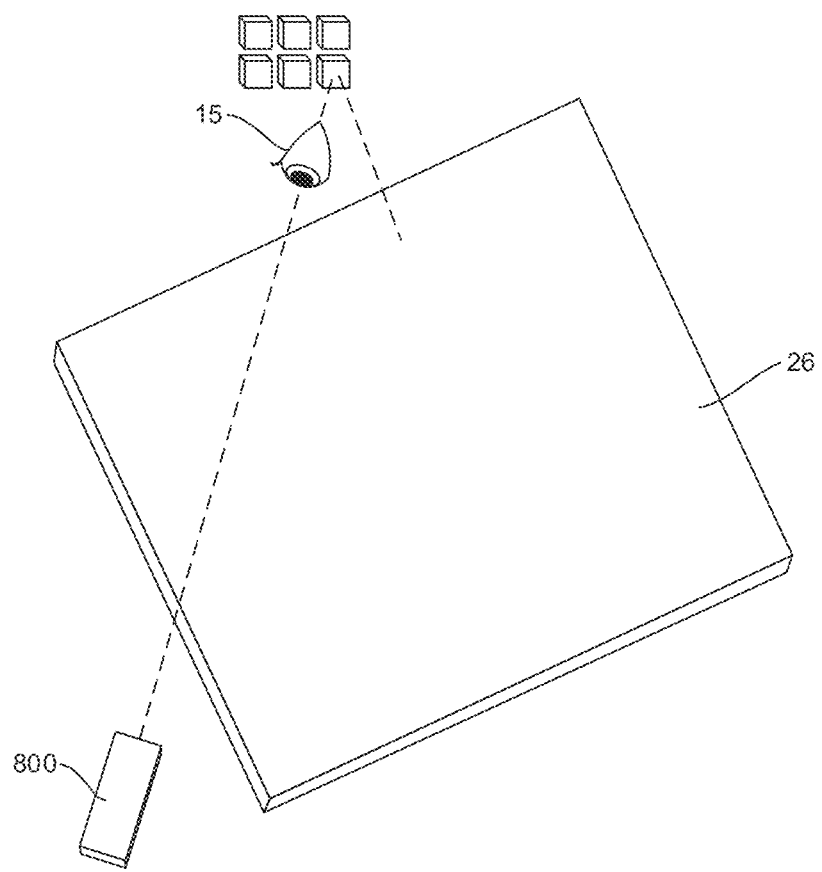

While FIGS. 1 and 6 show a transmissive system, FIG. 8 shows that a laser 800 may be used to sequentially irradiate each of a series of eyeball poses 802 (schematically shown as rectangles) in a reflective arrangement to encode the respective codes onto the film 26.

It may now be appreciated that once the film 26 has been encoded as described above, when another light beam such as a reflection of infrared (IR) light such as from a lower power laser or light emitting diode (LED) subsequently illuminates a human eye and is reflected onto the film, the light beam will illuminate the region of film that was encoded by the encoding laser 12 when the reference eyeball was in the same relative orientation/position to the film 26 as the subsequent eyeball is in. The light beam in turn represents the location of the person's eye, as IR light predominantly will reflect from the pupil.

Figure 9:
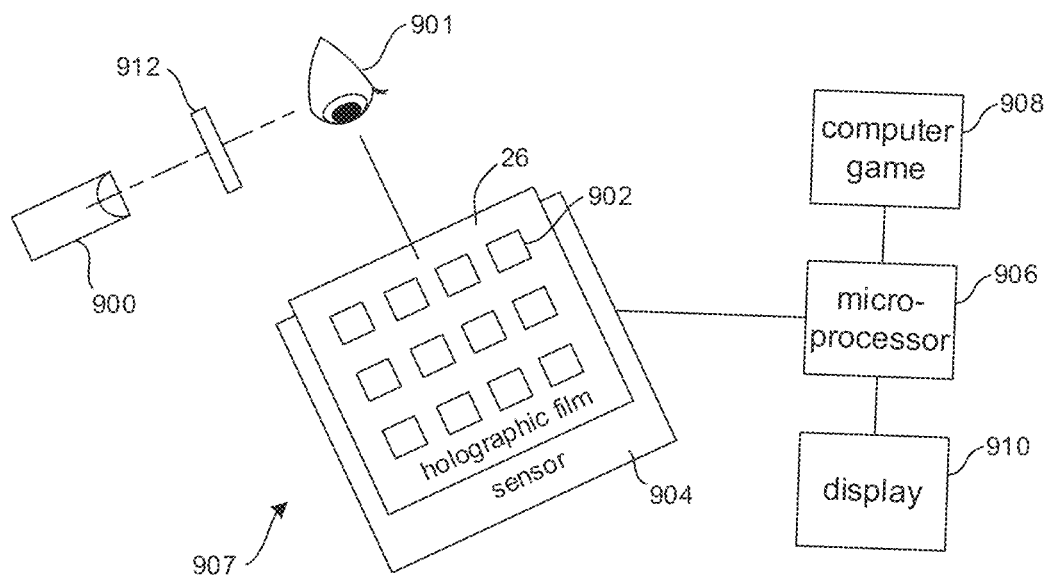
FIG. 9 illustrates how the pre-recorded holographic film is used to detect eye position, with a block diagram of an illuminator such as a reflection from a person's eye of an IR laser illuminating the holographic film with emissions from the film being detected by a sensor.

FIG. 9 illustrates an indicator light source 900 (with adjustable polarizer not shown) illuminating a human eye 901, with the reflection from the eye in turn illuminating one of plural encoded regions 902 on the film 26, with each region 902 encoding a unique robust code that is correlated to a respective pose of the reference eye as described above. The light source 900 may be, e.g., an ultra low power IR laser or light emitting diode. A sensor 904 such as but not limited to a charge-coupled device (CCD), complementary metal-oxide semiconductor (CMOS) detector, or photodiode array detector senses light emitted from the film 26 (and, hence, the unique code of the region 902 that is illuminated) and sends a signal representative thereof to one or more processors 906, such as an application specific integrated circuit (ASIC) or microcontroller unit (MCU) embedded onto/into the sensor 904 to render a combined film/sensor assembly 907 with, in some implementations, an embedded processor 906. The sensor 904 may be a very high framerate (>1000 Hz), low resolution (<64×64 pixels) sensor.

Note that the entire eyeball can reflect and interfere with the low power illumination light (e.g., infrared laser light), bouncing back to the holographic film 26. The film 26, if desired, can be segmented into the regions 902 to match the sensor 904 pixels on a one-to-one basis with a region 902 being overlaid onto a camera pixel. Each region 902 can contain the encoded reference interference pattern(s) that produce a strong correlation to a reference position/angle of the eye. Constructive or destructive interference can be used to provide the correlation along the lines of the principles of Holographic Interferometry.

The processor 906 can execute image recognition to determine which unique code is received and access the data structure shown in FIG. 7 to correlate the code to a pose of the eye 901 with respect to the film 26, such as an X-Y location in Cartesian coordinates. The processor 906 may execute a software-based computer game 908 and output demanded images from the game 908 onto a display 910, with game execution (and, hence, the demanded images) using, if desired, the eye pose to alter the game images. This is amplified on further below.

The indicator light source 900 may be an infrared (IR) laser. In some embodiments the wavelength of the light emitted by the indicator light source 900 may be greater than 1,000 nanometers, e.g., 1,440 nm to ensure that a game player does not see the laser light. The laser may be pulsed using a pulse repetition rate (PRR) that uniquely identifies the laser from other nearby indicator lasers. The laser may be modulated at a very high carrier frequency, e.g., in excess of one megahertz to increase the uniqueness of the light compared to other light sources like sunlight.

If desired, in some example implementations an encoding holographic film 912 may be placed between the light source 900 and film 26 (in the example shown, in the light path from the light source 900 to the eye 901) to provide a more consistent and defined interference pattern on the decoding film 26/sensor 904. By identifying the various light intensities that fall on the sensor 904, the position/angle of the eye can be determined.

Figure 10:
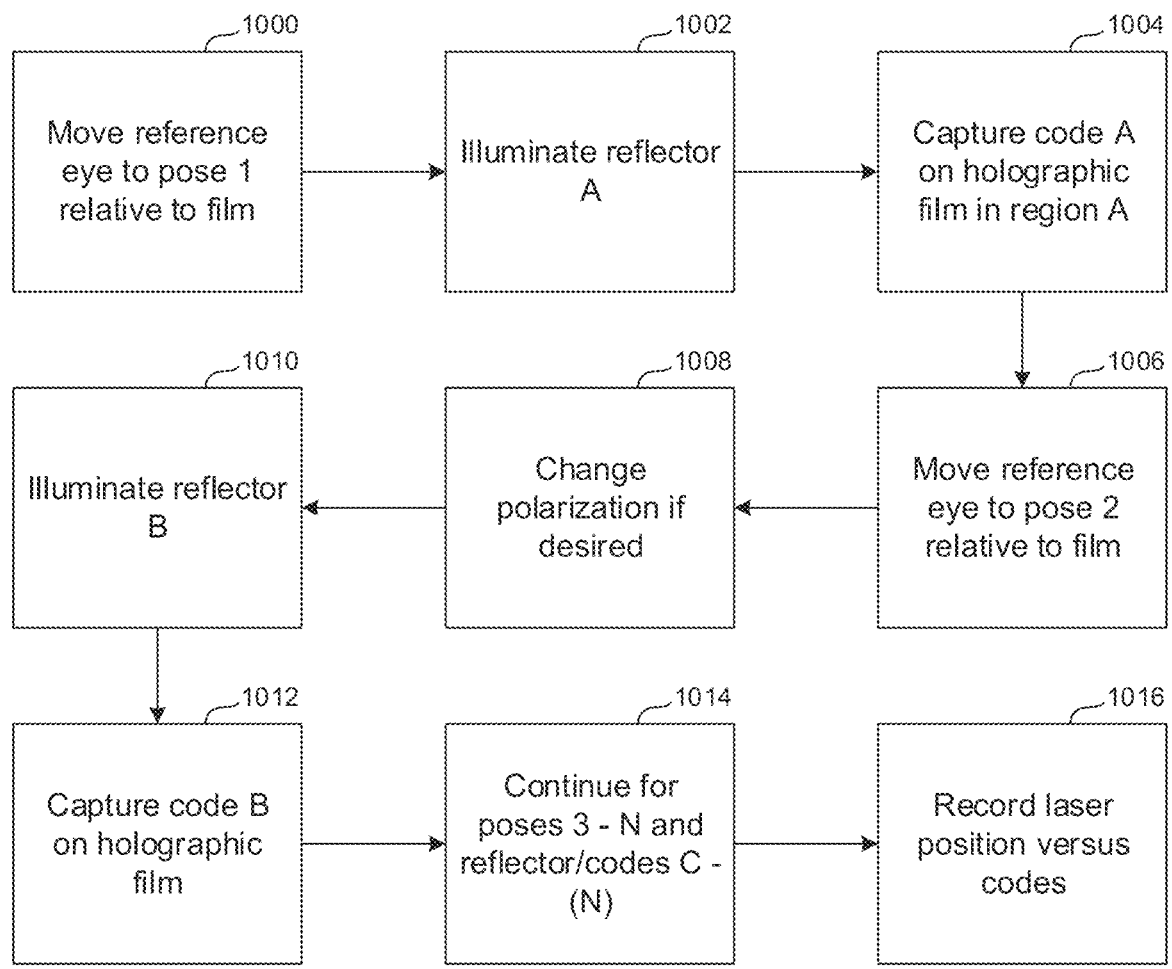

FIG. 10 shows the logic of the encoding technique described above while FIG. 11 shows the logic of the subsequent eye location determination technique, with some or all of the logic steps being controlled by any of the processors described herein. Commencing at block 1000, the reference eyeball is rotated/moved to the first pose relative to the film 26 and activated to illuminate a first reflector A at block 1002. The code is captured or encoded at block 1004 on the holographic film 26 in a first region A of the film (region 24 in FIGS. 1 and 6). This is achieved by the holographic recording process (for example, exposure of a photopolymer film to laser light).

Proceeding to block 1006 the reference eyeball is rotated to the next pose relative to the film 12, and if desired its polarization is changed at block 1008 for reasons explained above. A second reflector B is illuminated by the laser at block 1010 and its code captured (encoded) in the film 26 at block 1012. The described process of rotating the reference eyeball, changing polarization if desired, and successively illuminating reflectors continues at block 1014 for subsequent locations 3, . . . N to encode subsequent respective unique reflector codes C, . . . N onto the film 26, with each code being recorded and correlated to the respective location information of the reference eyeball at block 1016.

In examples, a silver halide crystal photo polymer holographic film is used.

Note that a mechanical eye of known properties may be used as the reference eyeball. Note that an encoding pattern such as any shown in FIGS. 2-5 and described above may be selected that is easily detectable and that increases the signal to noise ratio of the decoding process. The pattern may be based on the geometry of the eye. Preferably, the holographic film effectively compensates so that only light reflected off a pupil is clearly defined. An anti-distortion pattern may be used, and the pattern may be designed so that the "bump" of the iris is more in focus. The film may be exposed multiple times to increase the number of encodings that be recorded.

Figure 11:
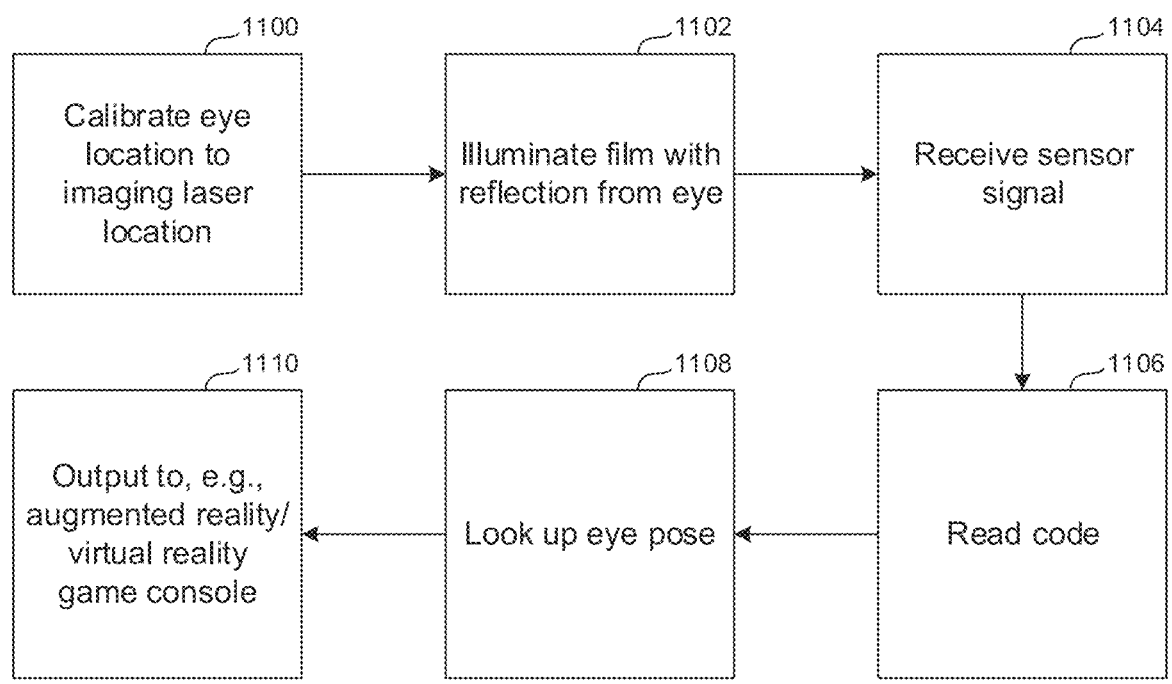
FIG. 11 is a flow chart of example logic for reading the codes on the film.

Recalling the subsequent eye location determination system of FIG. 9 and turning now to related FIG. 11, at block 1100, if desired the eye or eyes of a person as illuminated by the indicator light source 900 is calibrated to a location relative to the film 26 to approximate that of the reference eyeball in the earlier encoding process. This may be done, e.g., by instructing a user to mount the indicator light source at a certain point or location, e.g., on the top middle of a display on which a computer game is to be displayed and look in a specified direction, e.g., straight ahead. This calibration location may be supplied to a computer game.

Proceeding to block 1102, the film 26 is illuminated with light reflected from the eye from the indicator light source 900. The sensor 904 senses the resultant unique robust code pattern of light emitted from the film and its signal representative thereof is received at block 1104. Image recognition is applied to the signal to recognize the code at block 1106, which is then used at block 1108 as entering argument to, e.g., the data structure of FIG. 7 to return the corresponding pose of the eye with respect to the film, such as the X-Y location of the pupil of the eye relative to the location of surrounding eye tissue. This pose may be output at block 1110 to an AR or VR computer game console or other electronic device that uses eye tracking for various purposes. In some embodiments, instead of or in addition to a lookup table, the processor (e.g., an embedded ASIC/MCU) can use a pre-trained convolutional neural network classifier to robustly interpret many variations of the binary patterns for conversion to X, Y positions.

In example embodiments, each holographic film may be established by plural sub-films.

Various eye shapes and distances between pupils may be adapted for, with variations on the shape of the eye being be encoded onto the film. After calibration, a person whose eyes are to be tracked may elect to wear contact lenses, which may distort the current system, so the eyes may be imaged with contacts and without to calibrate for contact wearing. Beam steering may be affected by changing an angle of a mirror reflecting light from the eye to the sensor based on whether the person has contacts, how hard the contacts are, etc. To account for jostling during imaging, a tilting mirror can be adjusted until a highest signal is detected. Other forms adjustments can be used to ensure the light reflected from the eye falls onto the sensor to ensure accurate eye tracking via the present application.

A movable film/sensor assembly 907 may be implemented by a VR or AR headset such as the ones shown in FIGS. 12A and 14 and described further below. A single headset may include multiple assemblies that can be illuminated by reflections from respective eyes. Since the arrangement of plural film/sensor assemblies on a headset is known, their relative locations with respect to each other also are known.

Figure 12:
FIG. 12 illustrates that the object bearing the film/substrate assembly can be a hand-held game controller.
Figure 12A:
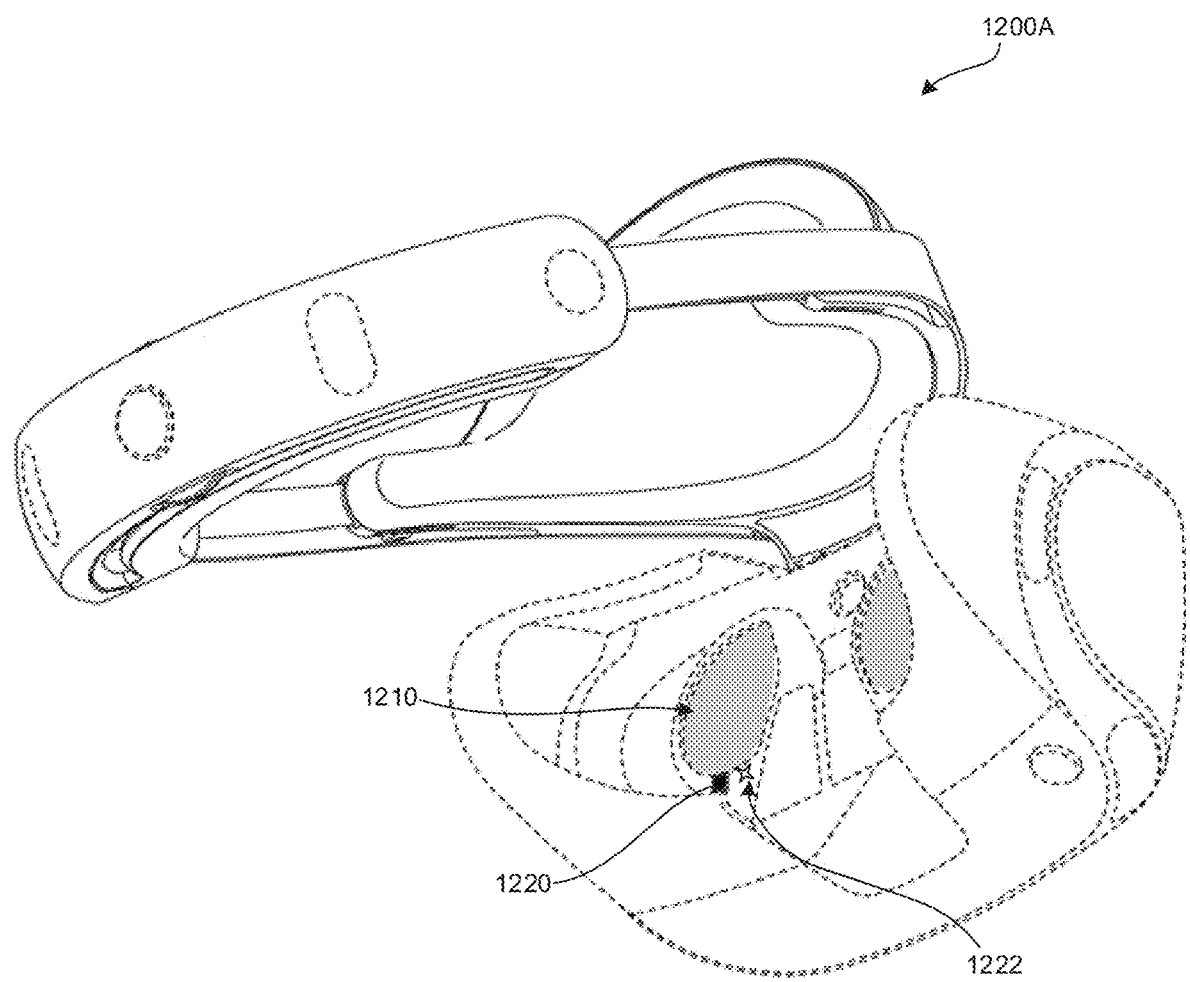
FIG. 12A illustrates that the object bearing the film/substrate assembly can be a Head Mounted Display.

Or, the movable film/sensor assembly 907 may be implemented by a game controller such as the controller 1200 shown in FIG. 12 or a head-mounted display 1200A as shown in FIG. 12A. In FIG. 12A, the HMD 1200A comprises lenses 1210 and at least one holographic decoding film and CMOS sensor assembly 1220 consistent with principles above. At least one laser light source (and optionally holographic encoding film) assembly 1222 is positioned to illuminate the eye, reflections of which impinge upon the holographic decoding film and CMOS sensor assembly 1220.

Figure 13:
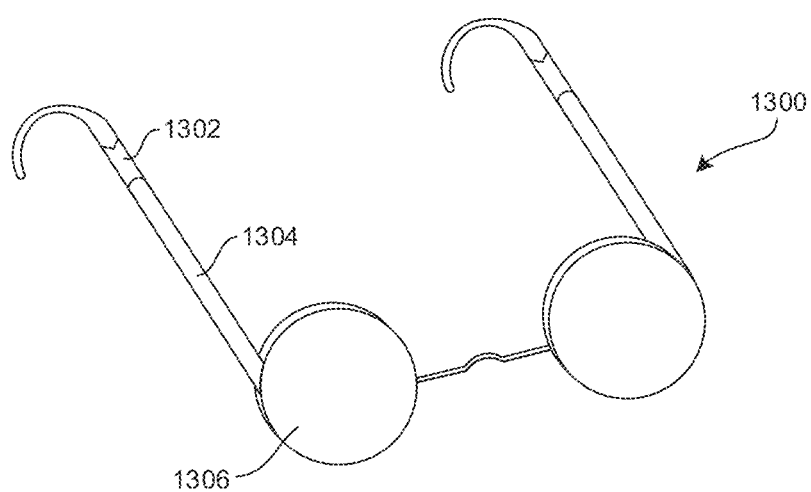
FIG. 13 illustrates that the object bearing the film/substrate assembly can be a glasses-like headset, schematically showing the illuminator with a light pipe.

Yet again, the movable film/sensor assembly 907 may be implemented by an eyeglasses-type frame 1300 (FIG. 13). A laser or other light source (e.g., IR LED) 1302 may be mounted in the frame and a light pipe 1304 may be used to direct laser light onto glasses-type displays 1306. Yet again, the film/CMOS assembly 907 may be implemented in a wristwatch, mobile phone, tablet, laptop or any of the example devices such as the device shown in, e.g., FIG. 14.

Each movable film/sensor assembly 907 can determine one or more eye locations as described above and wirelessly report the location to the game processor. Or, the assembly 907 can simply send a signal representing the unique code being illuminated to the game processor for derivation of the location by the game processor. Regardless, the game processor may then know, for example, the location of a player's eyes and tailor presentation accordingly.

Now referring to FIG. 14, an example system 1400 is shown, which may include one or more of the example devices mentioned below in accordance with present principles. The first of the example devices included in the system 1410 is a consumer electronics (CE) device such as an audio video device (AVD) 1412 such as but not limited to an Internet-enabled TV with a TV tuner (equivalently, set top box controlling a TV). However, the AVD 1412 alternatively may be an appliance or household item, e.g. computerized Internet enabled refrigerator, washer, or dryer. The AVD 1412 alternatively may also be a computerized Internet enabled ("smart") telephone, a tablet computer, a notebook computer, a wearable computerized device such as e.g. computerized Internet-enabled watch, a computerized Internet-enabled bracelet, other computerized Internet-enabled devices, a computerized Internet-enabled music player, computerized Internet-enabled head phones, a computerized Internet-enabled implantable device such as an implantable skin device, etc. Regardless, it is to be understood that the AVD 1412 is configured to undertake present principles (e.g. communicate with other CE devices to undertake present principles, execute the logic described herein, and perform any other functions and/or operations described herein).

Accordingly, to undertake such principles the AVD 1412 can be established by some or all of the components shown in FIG. 14. For example, the AVD 1412 can include one or more displays 1414 that may be implemented by a high definition or ultra-high definition "4K" or higher flat screen and that may be touch-enabled for receiving user input signals via touches on the display. The AVD 1412 may include one or more speakers 1416 for outputting audio in accordance with present principles, and at least one additional input device 1418 such as e.g. an audio receiver/microphone for e.g. entering audible commands to the AVD 1412 to control the AVD 1412. The example AVD 1412 may also include one or more network interfaces 1420 for communication over at least one network 1422 such as the Internet, an WAN, an LAN, etc. under control of one or more processors 1424 including. A graphics processor 1424A may also be included. Thus, the interface 1420 may be, without limitation, a Wi-Fi transceiver, which is an example of a wireless computer network interface, such as but not limited to a mesh network transceiver. It is to be understood that the processor 1424 controls the AVD 1412 to undertake present principles, including the other elements of the AVD 1412 described herein such as e.g. controlling the display 1414 to present images thereon and receiving input therefrom. Furthermore, note the network interface 1420 may be, e.g., a wired or wireless modem or router, or other appropriate interface such as, e.g., a wireless telephony transceiver, or Wi-Fi transceiver as mentioned above, etc.

In addition to the foregoing, the AVD 1412 may also include one or more input ports 1426 such as, e.g., a high definition multimedia interface (HDMI) port or a USB port to physically connect (e.g. using a wired connection) to another CE device and/or a headphone port to connect headphones to the AVD 1412 for presentation of audio from the AVD 1412 to a user through the headphones. For example, the input port 1426 may be connected via wire or wirelessly to a cable or satellite source 1426a of audio video content. Thus, the source 1426a may be, e.g., a separate or integrated set top box, or a satellite receiver. Or, the source 1426a may be a game console or disk player containing content that might be regarded by a user as a favorite for channel assignation purposes described further below. The source 1426a when implemented as a game console may include some or all of the components described below in relation to the CE device 1444.

The AVD 1412 may further include one or more computer memories 1428 such as disk-based or solid-state storage that are not transitory signals, in some cases embodied in the chassis of the AVD as standalone devices or as a personal video recording device (PVR) or video disk player either internal or external to the chassis of the AVD for playing back AV programs or as removable memory media. Also, in some embodiments, the AVD 1412 can include a position or location receiver such as but not limited to a cellphone receiver, GPS receiver and/or altimeter 1430 that is configured to e.g. receive geographic position information from at least one satellite or cellphone tower and provide the information to the processor 1424 and/or determine an altitude at which the AVD 1412 is disposed in conjunction with the processor 1424. However, it is to be understood that that another suitable position receiver other than a cellphone receiver, GPS receiver and/or altimeter may be used in accordance with present principles to e.g. determine the location of the AVD 1412 in e.g. all three dimensions.

Continuing the description of the AVD 1412, in some embodiments the AVD 1412 may include one or more cameras 2632 that may be, e.g., a thermal imaging camera, a digital camera such as a webcam, and/or a camera integrated into the AVD 1412 and controllable by the processor 1424 to gather pictures/images and/or video in accordance with present principles. Also included on the AVD 1412 may be a Bluetooth transceiver 1434 and other Near Field Communication (NFC) element 1436 for communication with other devices using Bluetooth and/or NFC technology, respectively. An example NFC element can be a radio frequency identification (RFID) element.

Further still, the AVD 1412 may include one or more auxiliary sensors 1437 (e.g., a motion sensor such as an accelerometer, gyroscope, cyclometer, or a magnetic sensor, an infrared (IR) sensor, an optical sensor, a speed and/or cadence sensor, a gesture sensor (e.g. for sensing gesture command), etc.) providing input to the processor 1424. The AVD 1412 may include an over-the-air TV broadcast port 1438 for receiving OTA TV broadcasts providing input to the processor 1424. In addition to the foregoing, it is noted that the AVD 1412 may also include an infrared (IR) transmitter and/or IR receiver and/or IR transceiver 1442 such as an IR data association (IRDA) device. A battery (not shown) may be provided for powering the AVD 1412.

Still referring to FIG. 14, in addition to the AVD 1412, the system 1400 may include one or more other CE device types. In one example, a first CE device 1444 may be used to send computer game audio and video to the AVD 1412 via commands sent directly to the AVD 1412 and/or through the below-described server while a second CE device 1446 may include similar components as the first CE device 1444. In the example shown, the second CE device 1446 may be configured as a VR headset worn by a player 1447 as shown. In the example shown, only two CE devices 1444, 1446 are shown, it being understood that fewer or greater devices may be used. For example, principles below discuss multiple players 1447 with respective headsets communicating with each other during play of a computer game sourced by a game console to one or more AVD 1412, as an example of a multiuser voice chat system.

In the example shown, to illustrate present principles all three devices 1412, 1444, 1446 are assumed to be members of an entertainment network in, e.g., a home, or at least to be present in proximity to each other in a location such as a house. However, present principles are not limited to a particular location, illustrated by dashed lines 1448, unless explicitly claimed otherwise. Any or all of the devices in FIG. 14 can implement any one or more of the lasers, films, and sensors described previously.

The example non-limiting first CE device 1444 may be established by any one of the above-mentioned devices, for example, a portable wireless laptop computer or notebook computer or game controller (also referred to as "console"), and accordingly may have one or more of the components described below. The first CE device 1444 may be a remote control (RC) for, e.g., issuing AV play and pause commands to the AVD 1412, or it may be a more sophisticated device such as a tablet computer, a game controller communicating via wired or wireless link with the AVD 1412, a personal computer, a wireless telephone, etc.

Accordingly, the first CE device 1444 may include one or more displays 1450 that may be touch-enabled for receiving user input signals via touches on the display. The first CE device 1444 may include one or more speakers 1452 for outputting audio in accordance with present principles, and at least one additional input device 1454 such as e.g. an audio receiver/microphone for e.g. entering audible commands to the first CE device 1444 to control the device 1444. The example first CE device 1444 may also include one or more network interfaces 1456 for communication over the network 1422 under control of one or more CE device processors 1458. A graphics processor 1458A may also be included. Thus, the interface 1456 may be, without limitation, a Wi-Fi transceiver, which is an example of a wireless computer network interface, including mesh network interfaces. It is to be understood that the processor 1458 controls the first CE device 1444 to undertake present principles, including the other elements of the first CE device 1444 described herein such as e.g. controlling the display 1450 to present images thereon and receiving input therefrom. Furthermore, note the network interface 1456 may be, e.g., a wired or wireless modem or router, or other appropriate interface such as, e.g., a wireless telephony transceiver, or Wi-Fi transceiver as mentioned above, etc.

In addition to the foregoing, the first CE device 1444 may also include one or more input ports 1460 such as, e.g., a HDMI port or a USB port to physically connect (e.g. using a wired connection) to another CE device and/or a headphone port to connect headphones to the first CE device 1444 for presentation of audio from the first CE device 1444 to a user through the headphones. The first CE device 1444 may further include one or more tangible computer readable storage medium 1462 such as disk-based or solid-state storage. Also in some embodiments, the first CE device 1444 can include a position or location receiver such as but not limited to a cellphone and/or GPS receiver and/or altimeter 1464 that is configured to e.g. receive geographic position information from at least one satellite and/or cell tower, using triangulation, and provide the information to the CE device processor 1458 and/or determine an altitude at which the first CE device 1444 is disposed in conjunction with the CE device processor 1458. However, it is to be understood that that another suitable position receiver other than a cellphone and/or GPS receiver and/or altimeter may be used in accordance with present principles to e.g. determine the location of the first CE device 1444 in e.g. all three dimensions.

Continuing the description of the first CE device 1444, in some embodiments the first CE device 1444 may include one or more cameras 1466 that may be, e.g., a thermal imaging camera, a digital camera such as a webcam, and/or a camera integrated into the first CE device 1444 and controllable by the CE device processor 1458 to gather pictures/images and/or video in accordance with present principles. Also included on the first CE device 1444 may be a Bluetooth transceiver 1468 and other Near Field Communication (NFC) element 1470 for communication with other devices using Bluetooth and/or NFC technology, respectively. An example NFC element can be a radio frequency identification (RFID) element.

Further still, the first CE device 1444 may include one or more auxiliary sensors 1472 (e.g., a motion sensor such as an accelerometer, gyroscope, cyclometer, or a magnetic sensor, an infrared (IR) sensor, an optical sensor, a speed and/or cadence sensor, a gesture sensor (e.g. for sensing gesture command), etc.) providing input to the CE device processor 1458. The first CE device 1444 may include still other sensors such as e.g. one or more climate sensors 1474 (e.g. barometers, humidity sensors, wind sensors, light sensors, temperature sensors, etc.) and/or one or more biometric sensors 1476 providing input to the CE device processor 1458. In addition to the foregoing, it is noted that in some embodiments the first CE device 1444 may also include an infrared (IR) transmitter and/or IR receiver and/or IR transceiver 1478 such as an IR data association (IRDA) device. A battery (not shown) may be provided for powering the first CE device 1444. The CE device 1444 may communicate with the AVD 1412 through any of the above-described communication modes and related components.

The second CE device 1446 may include some or all of the components shown for the CE device 1444. Either one or both CE devices may be powered by one or more batteries.

Now in reference to the afore-mentioned at least one server 1480, it includes at least one server processor 1482, at least one tangible computer readable storage medium 1484 such as disk-based or solid state storage, and at least one network interface 1486 that, under control of the server processor 1482, allows for communication with the other devices of FIG. 14 over the network 1422, and indeed may facilitate communication between servers and client devices in accordance with present principles. Note that the network interface 1486 may be, e.g., a wired or wireless modem or router, Wi-Fi transceiver, or other appropriate interface such as, e.g., a wireless telephony transceiver.

Accordingly, in some embodiments the server 1480 may be an Internet server or an entire server "farm", and may include and perform "cloud" functions such that the devices of the system 1400 may access a "cloud" environment via the server 1480 in example embodiments for, e.g., network gaming applications. Or, the server 1480 may be implemented by one or more game consoles or other computers in the same room as the other devices shown in FIG. 14 or nearby.

The methods herein may be implemented as software instructions executed by a processor, suitably configured application specific integrated circuits (ASIC) or field programmable gate array (FPGA) modules, or any other convenient manner as would be appreciated by those skilled in those art. Where employed, the software instructions may be embodied in a non-transitory device such as a CD ROM or Flash drive. The software code instructions may alternatively be embodied in a transitory arrangement such as a radio or optical signal, or via a download over the internet.

It will be appreciated that whilst present principals have been described with reference to some example embodiments, these are not intended to be limiting, and that various alternative arrangements may be used to implement the subject matter claimed herein.

What is claimed is:

1. An apparatus comprising:
   at least one holographic film with coded regions established by reflections from a human eye of light;
   the coded regions being correlated to respective poses of the human eye;
   at least one sensor to sense light from areas of the film illuminated by reflection of light from a person's eye and representing at least one of the coded regions; and
   at least one decoder to decode signals from the sensor to return a respective pose of the eye.

2. The apparatus of claim 1, wherein light from the reflection of light from a person's eye is infrared (IR).

3. The apparatus of claim 1, wherein the sensor comprises at least one complementary metal-oxide-semiconductor (CMOS) sensor.

4. The apparatus of claim 1, wherein the decoder comprises at least one processor.

5. The apparatus of claim 4, wherein the processor comprises at least one application specific integrated circuit (ASIC).

6. The apparatus of claim 4, wherein the processor comprises at least one microcontroller unit (MCU).

7. The apparatus of claim 4, wherein the processor is embedded onto/into the sensor.

8. An apparatus, comprising:
   at least one holographically recorded film having plural coded regions, each coded region representing a respective code;
   at least one sensor to sense light from at least one coded region of the film illuminated by a reflection from an eye; and
   at least one decoder configured for decoding signals from the sensor representing the at least one coded region to return a respective pose of the eye.

9. The apparatus of claim 8, wherein the codes comprise respective plural different splotches.

10. The apparatus of claim 8, wherein the codes comprise respective plural different lines.

11. The apparatus of claim 8, wherein the codes comprise respective plural different bar codes.

12. The apparatus of claim 8, wherein the codes comprise respective plural different quick response (QR) codes.

13. The apparatus of claim 8, wherein the light source comprises at least one light emitting diode (LED).

14. The apparatus of claim 8, wherein the sensor comprises at least one complementary metal-oxide-semiconductor (CMOS) sensor.

15. The apparatus of claim 8, wherein the decoder comprises at least one application specific integrated circuit (ASIC).

16. The apparatus of claim 8, wherein the decoder comprises at least one microcontroller unit (MCU).

17. The apparatus of claim 8, wherein the decoder is embedded onto/into the sensor.

18. An apparatus, comprising:
   at least one holographically recorded film having plural coded regions, each coded region representing a respective code; and
   at least one means for correlating the coded regions to respective poses of an eye.

19. The apparatus of claim 18, comprising:
   at least one light source;
   at least one sensor to sense light emitted by the light source and reflected from a human eye onto at least one coded region of the film; and
   at least one decoder configured for correlating signals from the sensor representing the at least one coded region to return a respective pose of the eye.

20. The apparatus of claim 19, wherein the light from the light source is infrared (IR).

* * * * *